United States Patent [19]
Thoresen et al.

[11] Patent Number: 5,785,578
[45] Date of Patent: Jul. 28, 1998

[54] EQUIPMENT FOR THE GRINDING OF MATERIAL SAMPLES

[75] Inventors: Bjørn Thoresen, Oslo; Geir Thorkilsen, Erdal, both of Norway

[73] Assignee: Norsk Hydro a.s., Oslo, Norway

[21] Appl. No.: 592,343

[22] PCT Filed: Jun. 14, 1995

[86] PCT No.: PCT/NO95/00101

§ 371 Date: Feb. 7, 1996

§ 102(e) Date: Feb. 7, 1996

[87] PCT Pub. No.: WO95/34802

PCT Pub. Date: Dec. 21, 1995

[30] Foreign Application Priority Data

Jun. 15, 1994 [NO] Norway ............................ 942242

[51] Int. Cl.⁶ .................. B24B 49/00; B24B 51/00
[52] U.S. Cl. ................. 451/14; 451/5; 451/160; 451/158
[58] Field of Search .................. 451/14.5, 159.9, 451/160, 158, 273, 272, 264, 265, 274, 212, 199, 213

[56] References Cited

U.S. PATENT DOCUMENTS

| | | | |
|---|---|---|---|
| 2,869,292 | 11/1959 | Klugman | 451/273 |
| 3,534,506 | 10/1970 | Soong et al. | 451/159 |
| 3,653,854 | 4/1972 | Asano | 451/14 |
| 3,704,554 | 12/1972 | Laughman | 451/159 |
| 3,732,647 | 5/1973 | Stith | 451/158 |
| 4,760,668 | 8/1988 | Schlaefli | 451/273 |
| 5,035,087 | 7/1991 | Nishiguchi et al. | 451/14 |
| 5,245,793 | 9/1993 | Schmitz | 451/14 |
| 5,447,463 | 9/1995 | Schmitz | 451/14 |
| 5,542,874 | 8/1996 | Chikaki | 451/158 |

FOREIGN PATENT DOCUMENTS

| | | |
|---|---|---|
| 0 209 764 | 2/1987 | European Pat. Off. |
| 1 798 139 | 11/1971 | Germany. |
| 17 98 139 | 11/1971 | Germany. |
| 1 422 908 | 1/1976 | United Kingdom. |

OTHER PUBLICATIONS

Patent Abstracts of Japan, vol. 11, No. 76, M–569, abstract of JP, A, 61–230853 (Shibayama Kikai K.K.), 15 Oct. 1986.
Patent Abstracts of Japan, vol. 8, No. 136, M–340, abstract of JP, A, 59–37037 Tokyo Shibaura Denki K.K.), 29 Feb. 1984.

Primary Examiner—Timothy V. Eley
Assistant Examiner—Derris H. Banks
Attorney, Agent, or Firm—Wenderoth, Lind & Ponack, L.L.P.

[57] ABSTRACT

Equipment for the grinding of material samples includes a console and a frame structure. A turntable is mounted on the console and frame structure, with the turntable having a material sample holding portion capable of releasably holding a plurality of material samples thereon. At least one vertically movable grinding spindle is arranged above the turntable. A mechanism is further provided for laterally oscillating the turntable relative to the console and frame structure as well as relative to the at least one vertically movable grinding spindle. A programmable control unit is connected with the turntable, movable grinding spindle and mechanism for laterally oscillating the turntable for controlling grinding.

13 Claims, 4 Drawing Sheets

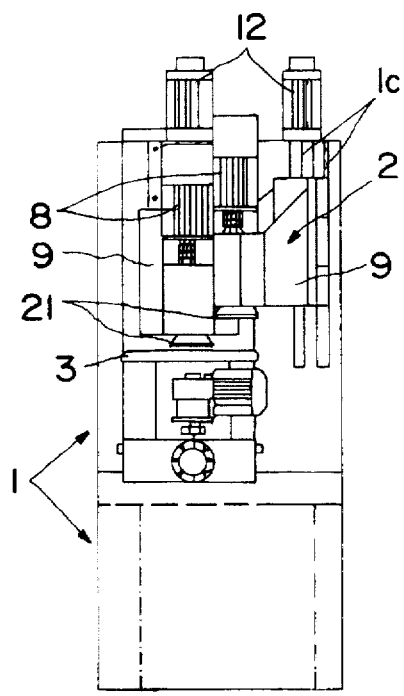
FIG. IA
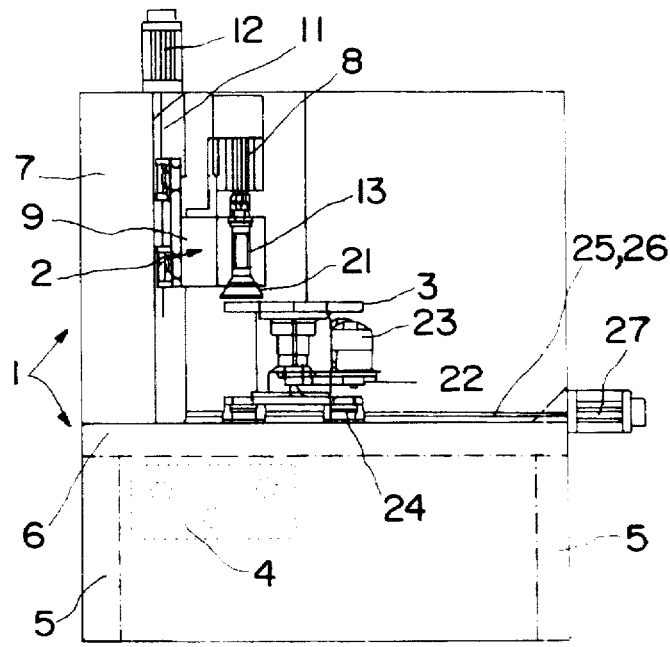
FIG. IB
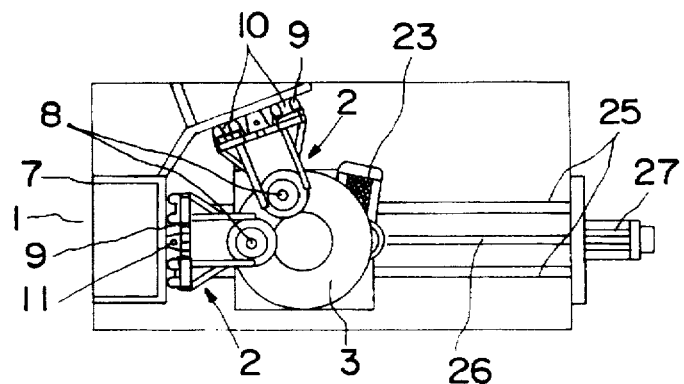
FIG. IC

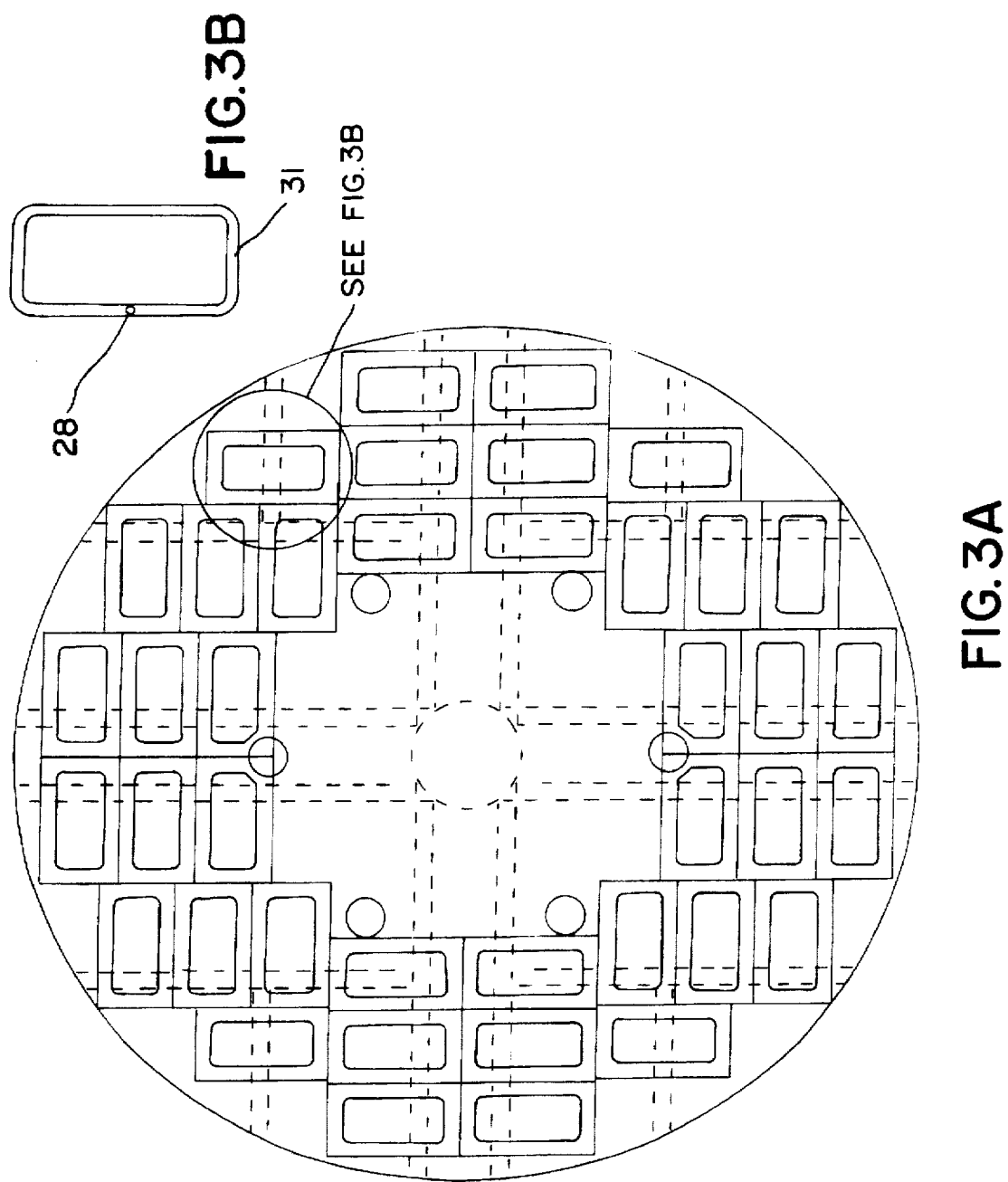

FIG. 4(a)
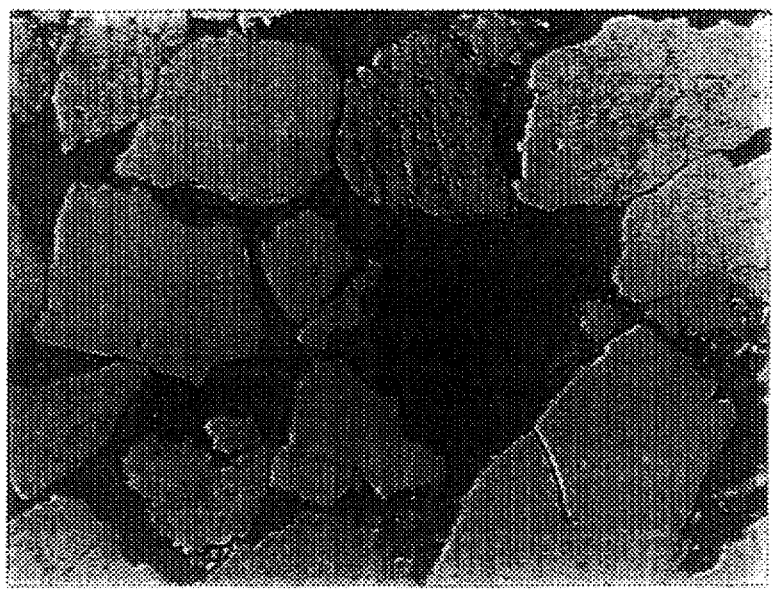
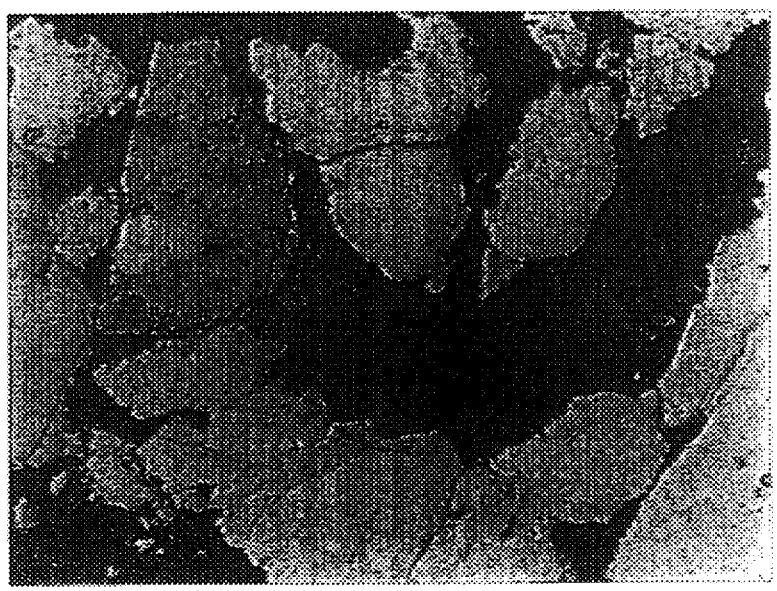
FIG. 4(b)

EQUIPMENT FOR THE GRINDING OF MATERIAL SAMPLES

BACKGROUND OF THE INVENTION

The present invention relates to equipment for the grinding of material samples, for instance microstructure grinding of a rock sample assembled on a microscope slide.

The extraction of oil and gas from an underground formation (rock) it is of basic importance to obtain knowledge of the nature of this formation. This is obtained inter alia by studying microstructures of the rock in question in a microscope to form an idea of the rock's porosity and structure. A grinding is produced at first by cutting a piece of the rock and then impregnating it. The impregnated piece is then surface ground before it is assembled on a microscope slide and finally ground.

The most common grinding method is based on so-called "patching". Silicon carbide grain in a water suspension is supplied to a rotary cast iron disk. The material samples (the microscope slide with the samples) are assembled with one or more rotary holders and are pressed towards the rotary cast iron disk. With this type of equipment and method the silicon carbide grains as such act as a grinding compound, and the thickness of the samples is reduced gradually to about 30 μm.

The know method and equipment is, however, encumbered with several disadvantages. Firstly, the grinding grains are pressed into the epoxy plastic in the material samples during the "patching" process and appear as black particles in the pores in the ground material samples. This, in the worst case, may make the samples unsuitable for further analyses. Secondly, the rotary cast iron disk may obtain an oblique surface during the grinding operation and have to be adjusted frequently. This involves considerably more work. The obliquity in the cast iron disk may also lead to considerably unevenness in the material samples in which case they could not be used for further testing.

A further disadvantage of the known equipment is that it requires supervision by an operator and is therefor expensive to us.

SUMMARY OF THE INVENTION

With the present invention there is provided equipment for grinding material samples where the disadvantages mentioned above are eliminated, i.e. which is essentially easier to use, provides essentially greater precision during the grinding operation, avoids the penetration of the grinding grains in the material samples, involves minimal contribution by the operator, gives an essentially finer and smoother surface of the finished, ground material samples, saves times in connection with later polishing of the surface of material samples, and has a greater grinding capacity.

The equipment according to the invention includes a rotating table (a turntable) on which the material samples are releasably provided. The grinding thereby takes place in at least one step by means of at least one vertically moveable grinding spindle arranged above the turntable.

BRIEF DESCRIPTION OF THE DRAWINGS

FIGS. 1(a)–(c) show (a) a front side view, (b) a side view and (c) a top view of grinding equipment in accordance with the invention;

FIGS. 3(a) and (b) show, as seen from the top and on an enlarged scale, a turntable according to the present invention and a detail thereof, respectively.

FIGS. 4 show two examples of material samples, which are ground by means of, in FIG. 4 (a), grinding equipment according to the invention, and in FIG. 4(b), known equipment by "patching" respectively.

DETAILED DESCRIPTION OF THE PREFERRED EMBODIMENT

Figure 2:
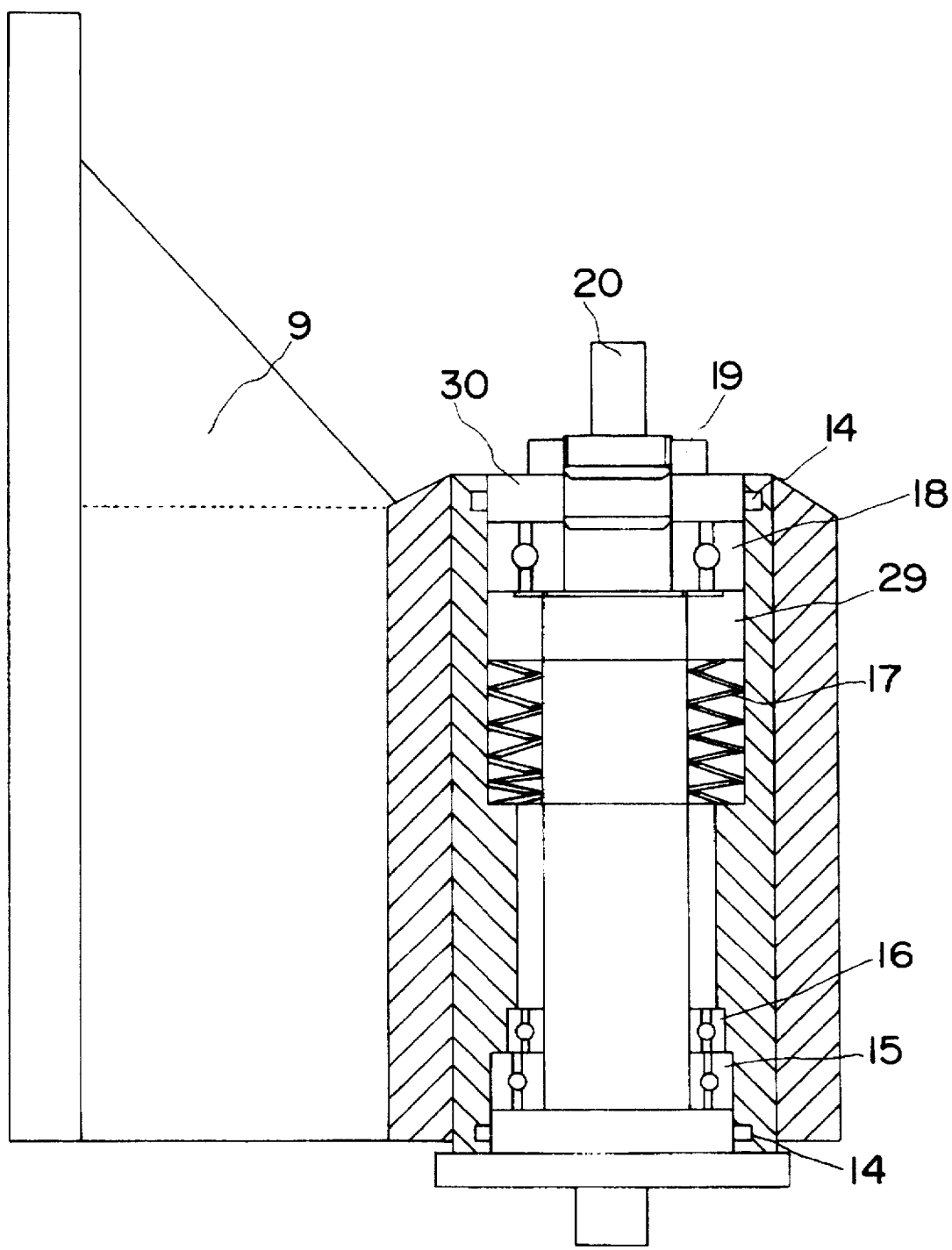
FIG. 2 shows, on a larger scale, a support for a grinding spindle included with the equipment of FIGS. 1(a)–(c)

The equipment according to the invention includes, as shown in FIG. 1, four main components, namely, a frame and console structure 1, a grinding spindle arrangement 2, a turntable 3 and a control unit 4.

The frame and console structure 1 is designed to absorb great amounts of energy, during the grinding operation when the equipment is used, and is therefore made of strong steel beams and stiffeners 5, 6 and 7 to ensure sufficient stability and prevent unevenness of the grinding samples. Concerning further details about the frame and console structure, such details lie within the competence of a person skilled in the art, and will therefore not be further described here.

The grinding spindle arrangement 2 comprises, as shown in FIG. 1, two grinder spindles provided above the turntable 3, one rough and one fine spindle, each being driven by an electric motor 8. Each spindle and motor unit 2, 8 are supported by a sledge or a carriage 9 which is movable in the vertical direction along rails 10 on the console structure.

Each carriage 9, with a spindle 2, can be moved up or down by means of a high precision nut and screw arrangement 11, which is operated by a servomotor 12. The equipment according to the invention is, as mentioned above, designed to be able to finely grind material samples to a thickness of 20–30 μm and with a precision of ±1 μm. To avoid deviations of the grindings by reason of thermal expansion, the grinding spindle is supported in a special support 13 on the sledge 9, which is further shown on an enlarged scale in FIG. 2. In detail are shown Teflon packings 14, angular contact ball bearings 15 and 16, cup springs 17, radial contact ball bearing 18, lock nut 19, spindle shaft 20 and a centering ring.

In the support are used bearings, as mentioned above, with different dimensions and ball numbers, because this will prevent the ball raceway from producing undesirable patterns in the grinding surface of the material samples. The cup springs produce a constant pressure toward the bearing 18 and respectively the low thrust bearings 15, 16, which results in that any overheating of the spindle does not create inaccuracy toward the grinding surface. The spindle shaft is, in other words, free to expand in the upward direction. The Teflon seal has low friction, which creates low heat generation in the spindle housing. As to the grinding spindles as such, they consist of diamond particles bound in a metal material formed as disks 21, and are preferably formed as a cup to obtain good cooling during the grinding operation. The use of diamond disks represents an essential advantage of the invention, since the material samples become entirely clean and free from unwanted particles in the structure of the ground material.

In FIGS. 4 are shown two examples of material samples which are ground by the means of, in FIG. 4(a), grinding equipment according to the invention, and in FIG. 4(b), known equipment by "patching", respectively. From FIG. 4(b) it follows that there are several unwanted particles in the material structure. The material samples shown in FIG. 4(a) have no such particles.

The turntable 3 (see FIGS. 1), which constitutes the third important element in the invention, comprises a circular disk which, via a belt 22 or the like, is driven by an electric motor 23. The disk 3 with the drive gear 22, 23 is arranged on a carriage, sledge or the like 24 which is movably provided on rails 25 on the frame structure 5. The carriage 24 can be suitably driven by means of a servomotor 27 via a nut and screw arrangement similar to the solution which is used for the raising and lowering of the grinding spindles 2.

By arranging the turntable 3 to be movable as mentioned above, there can be provided a combined oscillatory and rotary grinding motion for the material samples which give a smooth and exact (covering totally) grinding of these.

The material samples to be ground are releasably held in position on the turntable 3 by means of a vacuum. FIG. 3(a) shows, on an enlarged scale, a turntable 3 in accordance with the invention as seen from the top. The turntable is made of brass, free from material tension, and has several holes 28 communicating with grooves or recesses 31 (see FIG. 3(b)) which are arranged in a pattern at some distance from one another and which are connected to a vacuum source (not shown). Totally, the table has forty such holes with grooves, which can hold an equivalent number of such samples.

During the grinding process water is supplied to the turntable to cool the material samples via one or more nozzles provided above the table. This is not further shown in the figures.

The fourth important part which is included in the present invention is a programmable logic control (PLC) unit, which constitutes the control system 4. The operation of the PLC-unit can suitably take place via so-called "touch screen display" where different menus with touch buttons are used to control the grinding equipment. The whole control system is provided in connection with a control board arranged on the grinding equipment, or preferably on a separate control board, providing easy access for the operator.

The kind of PLC-unit which is used does not, as such, represent anything patentable, since it is available on the market, and therefore the technical solution of the PLC-unit will not be further described. However, in the following a brief description will be given with regard to how the grinding machine can be operated by means of the PLC-unit.

When a main switch is turned on, all the axes of the turntable and the grinding spindles will move to a zero point called "origo". Simultaneously the text "origo search" will be displayed at the operator display. When the equipment is ready to be used, a main menu will be displayed on the display. For instance, one can choose between automatic grinding of rock samples, automatic grinding of a sheet of glass or manual grinding.

By choosing manual grinding in the main menu, a sub menu will appear with choices related to the running of the turntable and choices as to which grinding motor it is desirable to use. If fine or rough grinding is chosen, another sub menu will appear where manual running of the grinding procedure is carried out. It is also possible here to get into and save (memorize) reference points, which later can be used for fully automatic grinding with the machine, i.e. by grinding a sample and by saving the reference points, the machine can automatically execute a repetition of the grinding procedure.

A choice of end positions for the oscillating movements of the turntable is performed on a separate menu. On this menu the speed for automatic grinding also can be programmed.

Before automatic grinding is chosen, the material samples are at first placed on the turntable, and the vacuum and cooling water is turned on. Thereafter automatic glass sample grinding or automatic rock sample grinding is chosen from the main menu. When this is done the respective sub menus appear and it is possible to start and stop the grinding procedure at any point in the program. The whole grinding procedure can be executed with rough and fine grinding and with simultaneous oscillation of the turntable until the grinding operation is finished. Then the turntable will move back to the starting point and the material samples are ready for further treatment and analyses.

As to the grinding operation, it should be noted that it is preferably to use two grinding wheels as described above, since the grinding time is reduced. In this case the material samples are rough-grinded to a suitable thickness at first, for instance 100 µm, with the rough grinding disk, before they are ground by the fine grinding disk to the desired thickness, for instance about 30 µm. The invention as defined in the claims is, however, not limited to two grinding disks, but can be provided with only one, or more than three disks of this kind.

We claim:

1. Equipment for grinding material samples, comprising:
a console and frame structure;
a turntable having a material sample holding portion, said turntable being rotatably mounted and movably mounted on said console and frame structure for rotation and for movement laterally in a direction parallel to said material sample holding portion;
a reciprocatory movement mechanism and a rotation mechanism connected to said turntable, said reciprocatory movement mechanism comprising a first motor and a transmission connected between said motor and said turntable capable of linearly moving said turntable on said console and frame structure, and said rotation mechanism comprising a second motor connected to said turntable capable of rotating said turntable;
at least one vertically moveable grinding spindle arranged above said turntable, each of said at least one vertically moveable grinding spindle comprising a grinding disk that is vertically moveable toward said material sample holding portion, a third motor connected to each of said at least one vertically moveable grinding spindle capable of rotating said grinding disk, and a fourth motor capable of vertically moving said grinding spindle; and
a programmable control unit connected with each of said first through fourth motors so as to be capable of controlling reciprocation and rotation of said turntable and rotation and vertical movement of said at least one grinding spindle.

2. The equipment of claim 1, wherein said at least one vertically moveable grinding spindle comprises two grinding spindles, one of which is a rough grinding spindle and the other of which is a fine grinding spindle.

3. The equipment of claim 2, wherein each said grinding disk comprises metal bound diamond particles.

4. The equipment of claim 1, wherein said grinding disk comprises metal bound diamond particles.

5. The equipment of claim 1, wherein said at least one grinding spindle comprises a carriage that is movable in a vertical direction along rails and said fourth motor comprises a servomotor connected to said carriage by a screw and nut arrangement.

6. The equipment of claim 1, wherein said turntable is mounted on a carriage, said carriage is mounted on rails, said first motor comprises a servomotor and said transmission comprises a screw and nut arrangement connected to said carriage and said servomotor.

7. The equipment of claim 6, wherein said turntable comprises a number of vacuum holes therein that are arranged along the circumference of said turntable and are connected to a vacuum source for holding material samples on said turntable.

8. The equipment of claim 1, wherein said at least one grinding spindle each comprises a grinding disk, a shaft having said grinding disk connected thereto, thrust bearings supporting said shaft, and a spring arrangement engaging said shaft such that said shaft is preset relative to said thrust bearings so that said shaft is free to undergo thermal expansion with out displacement of said grinding disk.

9. The equipment of claim 8, wherein said thrust bearings comprises two thrust bearings that are angular contact ball bearings having different diameters and numbers of balls.

10. The equipment of claim 1, wherein said grinding disk is capable of grinding material samples to a thickness of 20-30 micrometers, plus or minus one micrometer, under control of said control unit.

11. Equipment for grinding material samples, comprising:
a console and frame structure;
a turntable having a material sample holding portion, said turntable being rotatably mounted and movably mounted on said console and frame structure for rotation and for movement laterally in a direction parallel to said material sample holding portion;
a reciprocatory movement mechanism and a rotation mechanism connected to said turntable, said reciprocatory movement mechanism comprising a first motor and a transmission connected between said motor and said turntable capable of linearly moving said turntable, and said rotation mechanism comprising a second motor connected to said turntable capable of rotating said turntable;
at least one vertically moveable grinding spindle arranged above said turntable, each of said at least one vertically moveable grinding spindle comprising a grinding disk that is vertically moveable toward said material sample holding portion, a third motor connected to each of said at least one vertically moveable grinding spindle capable of rotating said grinding disk, and a fourth motor capable of vertically moving said grinding spindle; and
a programmable control means connected with each of said first through fourth motors for controlling reciprocation and rotation of said turntable and rotation and vertical movement of said at least one grinding spindle and capable of controlling said first through fourth motors such that reciprocation of said turntable, rotation of said turntable and rotation of said at least one grinding spindle can take place at the same time.

12. The equipment of claim 11, wherein said control means controls said first through said fourth motors in operation such that, when material samples are mounted on said turntable, said grinding disk is lowered into contact with the material samples by said fourth motor, and said first through third motors are operated simultaneously for simultaneous rotation of said turntable, reciprocation of said turntable, and rotation of said grinding disk.

13. The equipment of claim 11, wherein said grinding disk is capable of grinding material samples to a thickness of 20-30 micrometers, plus or minus one micrometer, under control of said control means.

* * * * *